United States Patent [19]

Kotylev et al.

[11] 4,158,806

[45] Jun. 19, 1979

[54] METHOD OF CHECKING THE STATE OF THE LINING OF A MELTING UNIT AND DEVICE FOR EFFECTING SAME

[76] Inventors: Alexandr M. Kotylev, ulitsa Malaya Schukinskaya, 58, kv. 17; Dmitry A. Gitgarts, ulitsa Petrozavodskaya, 17, korpus 2, kv. 209; Jury S. Ioffe, ulitsa Yaroslavskaya, 1/9, kv. 11; Alexandr A. Prostyakov, ulitsa Veshnyakovskaya, 35/26, kv. 66; Viktor I. Krizental, ulitsa Lavochkina, 54, korpus 2, kv. 163, all of Moscow, U.S.S.R.

[21] Appl. No.: 789,079

[22] Filed: Apr. 20, 1977

[51] Int. Cl.$^2$ ............................................. G01R 27/02
[52] U.S. Cl. .................................... 324/65 R; 324/64
[58] Field of Search ...................... 324/65 R, 65 P, 64

[56] References Cited

U.S. PATENT DOCUMENTS 3,735,253  5/1973  Seger ...................................... 324/64

*Primary Examiner*—Stanley T. Krawczewicz
*Attorney, Agent, or Firm*—Lackenbach, Lilling & Siegel

[57] ABSTRACT

The proposed method for checking the state of the lining of a melting unit consists of measuring the electric parameters of equal portions of the lining, located along the perimeter of the melting unit. This is followed by determining the arithmetic mean and the maximum value of these parameters and comparing the two. The result of the comparison is indicative of the state of the lining. According to the invention, the device for checking the state of the lining comprises electrodes which are uniformly installed on the lining along the perimeter of the melting unit. The electrodes are connected to the inputs of an information unit, which provides information about the state of the lining, as well as to the inputs of a maximum value unit for determining the maximum value of a parameter being measured. One output of the maximum value unit is connected to the first input of a comparison unit for comparing the maximum value and the arithmetic mean of the parameter being measured. Another output of the maximum value unit is connected to the first additional input of the information unit and to the input of a mean determining unit for determining the arithmetic mean of the parameter being measured. The output of the mean determining unit is connected to the second additional input of the information unit, to the second input of the comparison unit, and to a power source. Placed in series with the output of the comparison unit are an amplification unit and a signalling unit. The proposed method for checking the state of the lining of a melting unit and the device for effecting this method make it possible to increase the accuracy of checking overall wear and local damage of the lining.

10 Claims, 5 Drawing Figures

METHOD OF CHECKING THE STATE OF THE LINING OF A MELTING UNIT AND DEVICE FOR EFFECTING SAME

FIELD OF THE INVENTION

The present invention relates to the use of electric devices for checking the state of technological equipment and, more particularly, to a method for checking the state of the lining of a melting unit and a device for carrying out this method.

The invention is useful in checking and in control systems of melting units in all branches of industry where such units are used, including the metallurgical, machine-building, aircraft, automotive and other industries.

The invention is most advantageous for checking the state of the lining of induction furnaces. In such furnaces, the penetration of molten metal through the lining to the water-cooled inductor may cause an ejection of metal from the furnace, which may damage the equipment and, in some cases, take human lives.

The lining of induction furnaces is subjected to the effects of considerable temperature gradients and hydrostatic pressure of the metal, as well as to the chemical action on the part of the metal and slag, and the action of electrodynamic forces. All these factors destroy the lining by corroding and cracking it. As a result, the reliability and performance of melting units are largely determined by the durability of the lining and the possibility of checking its state during use when the furnace is heated.

DESCRIPTION OF THE PRIOR ART

There is known a method for checking the state of the lining of a melting unit, which consists in measuring an electrical parameter (the resistance) of the entire lining and producing an alarm signal if the value of the electrical parameter reaches a predetermined level.

However, this method is not sufficiently accurate, because the value of the parameter being measured depends not only on the degree of lining wear, but also on a number of other factors, including the temperature, humidity and density of the lining, the baked layer thickness, etc. A change in these factors may produce a spurious signal.

Lining wear may be uniform; it may also be localized over a limited area. Local damage is the most dangerous in that it occurs rapidly and cannot be visually detected. It must be pointed out in this connection that the method under review is not sensitive enough to detect local damage which covers a small portion of the lining. According to analytical data, the reduction factor K of the total resistance of the lining is related to the reduction factor m of the resistance of the damaged portion of the lining and the coefficient n of the ratio between the total lining area and the local damage area. This relationship is expressed as follows:

$$K = \frac{m-1}{n} + 1.$$

If molten metal penetrates through the lining over an area which is fifty times smaller than the total area of the lining, and the resultant decrease in the resistance of the damaged portion of the lining is ten-fold, the total resistance of the lining is only reduced by 20 percent. Such a change in the parameter being measured is also possible for to general wear in the lining and is, in fact, permissible by the existing standards. Hence, if the reduction factor K of the parameter being measured is assumed to be equal to 1.2, uniform general wear of the lining may be the cause of a spurious signal. If the factor K is more than 1.2, local damage of the lining may result in the penetration of molten metal to the inductor, without producing an alarm signal.

Clearly, the known method of checking the state of the lining makes it hard to accurately determine the actual state of the lining and set the level at which an alarm signal is to be given.

There is known a device intended for effecting the foregoing method of checking the state of the lining of a melting unit. The device comprises an electrode which is in contact with the metal, as well as cylindrical electrodes which are uniformly spaced over the outer surface of the lining. A power source is connected to the electrode which is in contact with the metal. Connected to the cylindrical electrodes is a measuring instrument which is electrically coupled to the power source.

The device under review checks the state of the lining by measuring the current flowing through the entire lining between the metal and the cylindrical electrodes, the magnitude of this current being inversely proportional to the resistance of the entire lining.

However, this device does not make it possible to detect a local damaged area, although it is absolutely necessary to know the exact location of this area in order to properly repair the lining.

There is known another device for checking the state of the lining of a melting unit. This device comprises a three-layer sensor arranged over the entire external surface of the lining. The sensor incorporates two thin metal layers separated by an insulating layer. The metal layers are connected to the opposite poles of a power source via two resistors and a signalling unit. An alarm signal is sent to the signalling unit if molten metal penetrates through the insulating layer, whereby one metal layer is shorted against the other, or if the insulating layer is overheated by the molten metal.

However, in the device under consideration, the sensor is too complicated and hard to install. The device has not found application in induction melting furnaces because of its complicated design and the necessity of increasing the thickness of the lining. An increase in the thickness of the lining reduces the efficiency of an induction furnace, as well as the power coefficient of the metal-inductor system.

There is known still another device for checking the state of the lining of a melting unit, which is intended to effect the above-mentioned method. The device comprises wire electrodes evenly spaced in the lining along the perimeter of the melting unit at a distance of from 5 to 8 mm from one another. The alternate electrodes are interconnected so that all the electrodes form two groups. One group of electrodes is directly connected to one pole of a power source, and the second group of electrodes is coupled to the opposite pole of the power source via the coil of an auxiliary relay which serves as a current amplifier. The contact of the auxiliary relay is connected to the input of a signalling unit. The signalling unit is constructed as an output relay with one of its contacts incorporated in a light and audio signalling circuit and its other contact placed in a power cutoff circuit of the melting unit.

The device under review measures current flowing through the whole of the lining between the two groups of electrodes. As the current reaches a certain magnitude, the auxiliary relay is brought into play and disconnects the power source of the melting unit and, at the same time, audio and light signals are produced.

However, the latter device is too complicated, for it includes a large number of wire electrodes spaced at a distance of from 5 to 8 mm from one another and a large number of electrodes is used to ensure the desired accuracy of checking the state of the lining.

Besides, the device does not elimate the possibility of a malfunction of the output relay due to thermal expansion of the wire electrodes.

It must also be borne in mind that the accuracy of the device depends upon the stability of the power source's voltage.

SUMMARY OF THE INVENTION

It is an object of the present invention to provide a method for checking the state of the lining of a melting unit and a device for effecting this method, which increases the accuracy of checking the state of linings subjected to uniform wear.

It is another object of the invention to raise the sensitivity for detecting local damaged areas of a lining.

It is still another object of the invention to make it possible to locate the place of penetration of the metal through the lining in case of local damage to the lining.

It is yet another object of the invention to simplify the device for checking the state of the lining of a melting unit.

Finally, it is an object of the invention to increase the reliability of melting units.

The foregoing objects of the present invention are attained by providing a method for checking the state of the lining of a melting unit, by measuring electrical parameters of the lining which are indicative of its state. The method is characterized, according to the invention, by the step of measuring electrical parameters of equal portions of the lining arranged along the perimeter of the melting unit; determining an arithmetic mean of the measured parameters and their maximum value; and comparing these values, the result of the comparison indicating the state of the lining.

The objects of the invention are also attained by providing a device for carrying out the foregoing method of checking the state of the lining of a melting unit, which comprises electrodes uniformly spaced on the lining along the perimeter of the melting unit and electrically coupled to a power source; an amplification unit whose output is connected to the input of a signalling unit; a maximum value unit for determining the maximum value of the parameter being measured; an information unit providing information about the state of the lining, whose outputs are connected to the electrodes; a mean determining unit for determining the arithmetic mean of the parameter being measured, whose input is connected to the first output of the maximum value unit and to the first additional input of the information unit, and whose output is connected to the second additional input of the information unit and to a power source; and a comparison unit for comparing the maximum value and the arithmetic mean of the parameter being measured, one of its inputs being connected to the second output of the maximum value unit measured, its other input being connected to the output of the mean determining unit, its output being connected to the amplification unit.

It is preferable that the maximum value unit comprise a group of resistors having equal resistance, one lead of each resistor being connected to one of the electrodes and the other leads being combined and connected to the first additional input of the information unit. The maximum value unit measured should also include a group of diodes whose cathodes are connected to respective electrodes, their plates or anodes being combined and connected to the first input of the comparison unit. The mean determining unit should be constructed as a resistor whose resistance is less than that of the resistors of the maximum value unit measured by a number of times equal to the number of electrodes. One lead of this resistor is connected to the combined leads of the resistors of the maximum value unit being measured; and the other lead of the resistor is connected to the power source, to the second input of the comparison unit, and to the second additional input of the information unit providing information about the state of the lining.

It is preferable that the comparison unit be built around control windings of a magnetic amplifier, connected in opposition, and that the amplification unit be built around the working windings of a magnetic amplifier.

In another embodiment, the comparison unit may be built around two zero-crossing detectors and a threshold element and the amplification unit may be constructed as a combination of three semiconductor amplifiers electrically coupled to the outputs of the zero-crossing detectors and the threshold element.

It is advisable that the electrodes be combined into groups, each having an equal number of electrodes. The number of inputs of the information unit and of the maximum value unit must be equal to that of the groups of electrodes and each input must be connected to one group of electrodes.

The proposed method for checking the state of the lining of a melting unit and the device for effecting this method are advantageous in many respects over the existing methods and devices.

In the first place, the proposed method improves the accuracy of evaluating general wear of the lining of a melting unit, because the parameter being monitored is the quotient of the division of the maximum value and the arithmetic mean of the electric conductivity of the portions of the lining. The parameter being measured depends very little upon such factors as the temperature, humidity or density of the lining, the baked layer thickness, etc.

Secondly, the proposed method and device improve the accuracy of detecting local damage of the lining, because checking involves the electric parameters of small portions of the lining, the areas of these portions being smaller than that of the entire lining.

In the third place, the method and device of this invention make it possible to pinpoint the damaged area of the lining due to the presence of the information unit which provides information on the state of the lining, which unit is connected to the maximum value unit, to the mean determining unit, and to the electrodes.

In the fourth place, the device according to the invention makes it possible to reduce the number of electrodes mounted on the outer surface of the lining. In one of the known devices, the electrodes are spaced at a distance of 5 to 8 mm; in the proposed device, they are spaced at equal distances of from 1.2 to 1.5 of the lining's thickness.

BRIEF DESCRIPTION OF THE DRAWINGS

Other objects and advantages of the present invention will become more apparent from the following detailed description of preferred embodiments thereof taken in conjunction with the accompanying drawings, wherein.

DETAILED DESCRIPTION OF THE INVENTION

Figure 1:
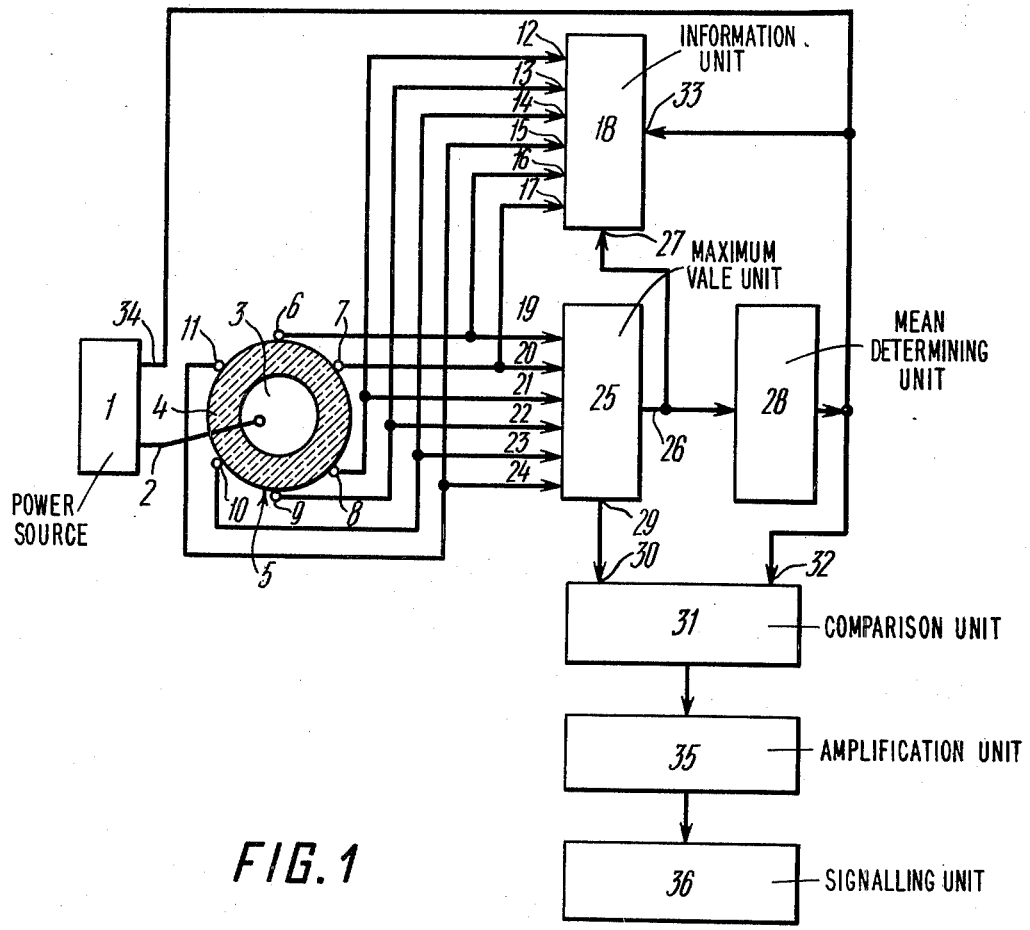
FIG. 1 is a block diagram of a device for effecting the method of checking the state of a lining of a melting unit, in accordance with the invention.

Referring now to the accompanying drawings, the device for effecting the proposed method for checking the state of the lining of a melting unit comprises a power source 1. One lead 2 of the power source 1 is connected to a metal element 3 inside a lining 4 of a melting unit 5. On the other surface of the lining 4 there are mounted electrodes 6, 7, 8, 9, 10 and 11 spaced at a distance equal to 1.4 of the lining's thickness. The electrodes 6,7,8,9, 10 and 11 are respectively connected to inputs 16, 17, 12, 13, 14, and 15 of an information unit 18 for providing information on the state of the lining 4, and to inputs 19, 20, 21, 22, 23 and 24 of a maximum value unit 25 for determining the maximum value of a parameter being measured. In the emodiment under review, the parameter being measured is the electric conductivity of individual portions of the lining 4. An output 26 of the maximum value unit 25 is connected to an input 27 of the information unit 18 and to an input of a mean determining unit 28 for determining the arithmetic mean of the parameter being measured. An output 29 of the maximum value unit 25 is connected to an input 30 of a comparison unit 31 for comparing the maximum value and the arithmetic mean of the parameter being measured. An output of the mean determining unit 28 is connected to an input 32 of the comparison unit 31, an input 33 of the information unit 18, and an output 34 of the power source 1. Placed in series with the output of the comparison unit 31 are an amplification unit 35 and a signalling unit 36.

The power source 1 comprises a transformer 37 (FIG. 2) having a primary winding 38 and secondary windings 39, 40 and 41. Connected to the windings 39 and 40 are bridge rectifiers 42 and 43 and capacitors 44 and 45, which serve as smoothing filters.

The maximum value 25 comprises resistors 46, 47, 48, 49, 50 and 51 having equal resistances, and diodes 52, 53, 54, 55, 56 and 57.

Leads 58, 59, 60, 61, 62 and 63 of the resistors 46, 47, 48, 49, 50 and 51, respectively, are connected to respective electrodes 6, 7, 8, 9, 10 and 11. Leads 64, 65, 66, 67, 68 and 69 are combined and connected to the output 26 of the maximum value unit and, consequently, to the input 27 of the information unit 18.

The cathodes of the diodes 52, 53, 54, 55, 56 and 57 are connected to respective electrodes 8, 9, 10, 11, 7 and 6. The plates or the anodes of the diodes 52, 53, 54, 55, 56 and 57 are combined and connected to the input 30 of the comparison output 29 of the maximum value unit and, consequently, to the unit 31.

A resistor 70 (FIG. 2) is provided to determine the arithmetic mean of the parameter being measured. The resistance of the resistor 70 is less than that of the resistors 46, 47, 48, 49, 50 and 51 by a number of times which is equal to the number of electrodes 6, 7, 8, 9, 10 and 11, i.e. in the present case, six times. A lead 71 of the resistor 70 is connected to the combined leads 64, 65, 66, 67, 68 and 69 of the resistors 46, 47, 48, 49, 50 and 51. A second lead 72 of the resistor 70 is connected to the power source 1, the input 33 of the information unit 18, and the input 32 of the comparison unit 31.

The information unit 18, which provides information on the state of the lining, comprises a voltmeter 73 and switches 74, 75 and 76 which serve to connect the voltemeter 73 to any of the resistors 46, 47, 48, 49, 50, 51 and 70. The switch 74 has six positions designated as I, II, III, IV, V and VI. Each of the switches 75 and 76 has two positions.

The comparison unit 31 comprises control windings 77 and 78 of a magnetic amplifier connected in opposition. Placed in series with the windings 77 and 78 are adjusting resistors 79 and 80 and an avalanche diode 81. The winding 77 is connected to the combined plates of the diodes 52, 53, 54, 55, 56 and 57 and coupled via the resistor 79 to the combined leads 64, 65, 66, 67, 68 and 69 of the resistors 46, 47, 48, 49, 50 and 51 of the maximum value unit 25. The winding 78 is connected to the lead 72 of the resistor 70 via the adjusting resistor 80.

The amplification unit 35 comprises working windings 82 and 83 of a magnetic amplifier and diodes 84 and 85 connected to said working windings 82 and 83 and to a bridge rectifier 86. The amplification unit 35 further includes a bias winding 87 connected to the rectifier 43 and an adjustable resistor 88.

The signalling unit 36 comprises two relays having windings 89 and 90 with respective contacts $89_1$, $90_1$, $90_2$ and $90_3$. The closing of the make contact $89_1$ switches on an indicating lamp 91, thus producing a visual alarm signal. The closing of the make contacts $90_1$ and $90_2$ switches on an indicating lamp 92 and an audio indicator, which may be a siren 93, whereby visual and audio alarm signals are produced. The opening of the break contact $90_3$ disconnects the power source (not shown) of the melting unit 5 when an alarm signal is produced.

The operation threshold of the above-mentioned relays is set with the aid of adjustable resistors 94 and 95 which are connected to the windings 89 and 90, respectively.

Figure 2:
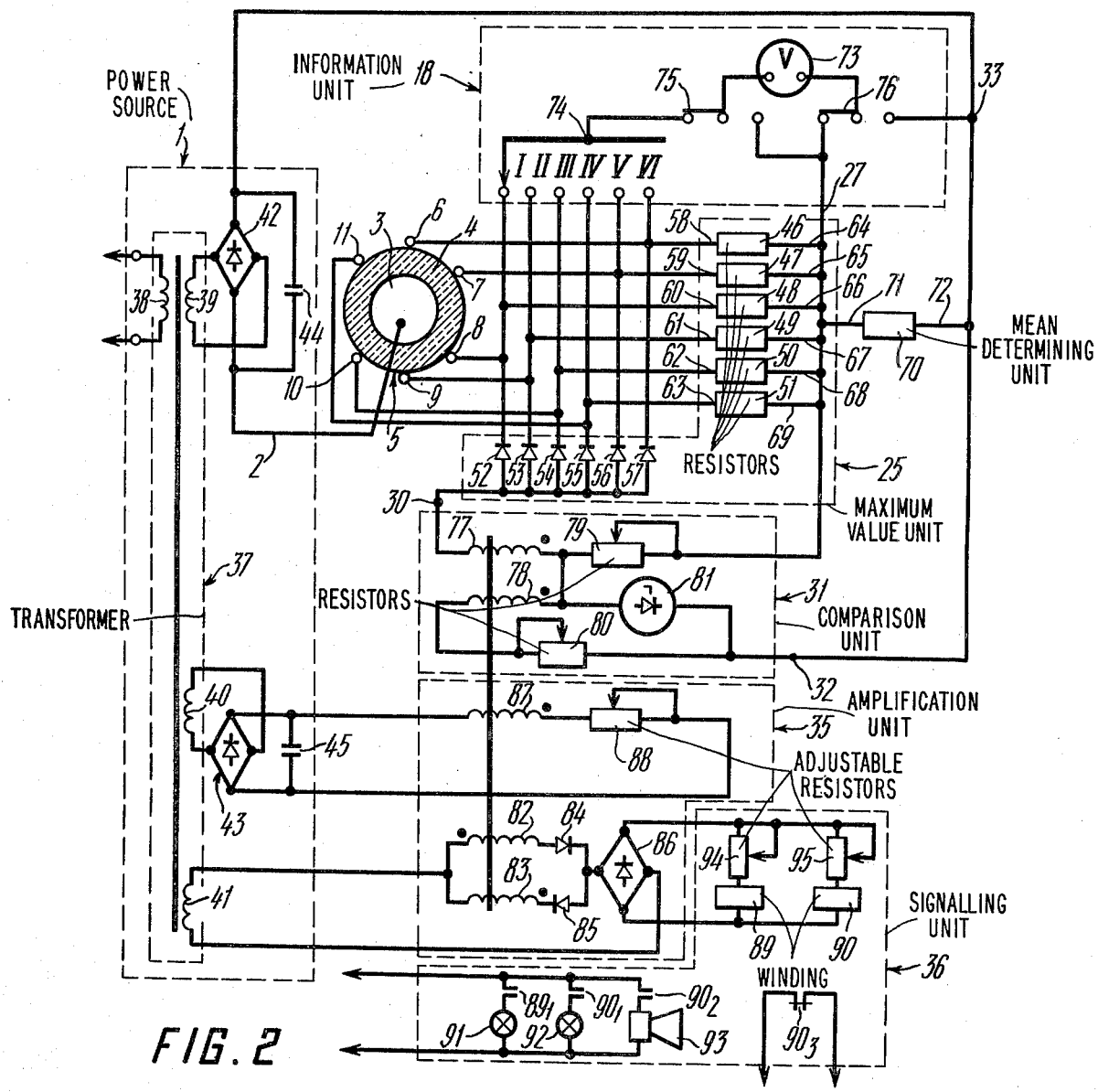
FIG. 2 is a schematic diagram of a device in accordance with the invention.
Figure 3:
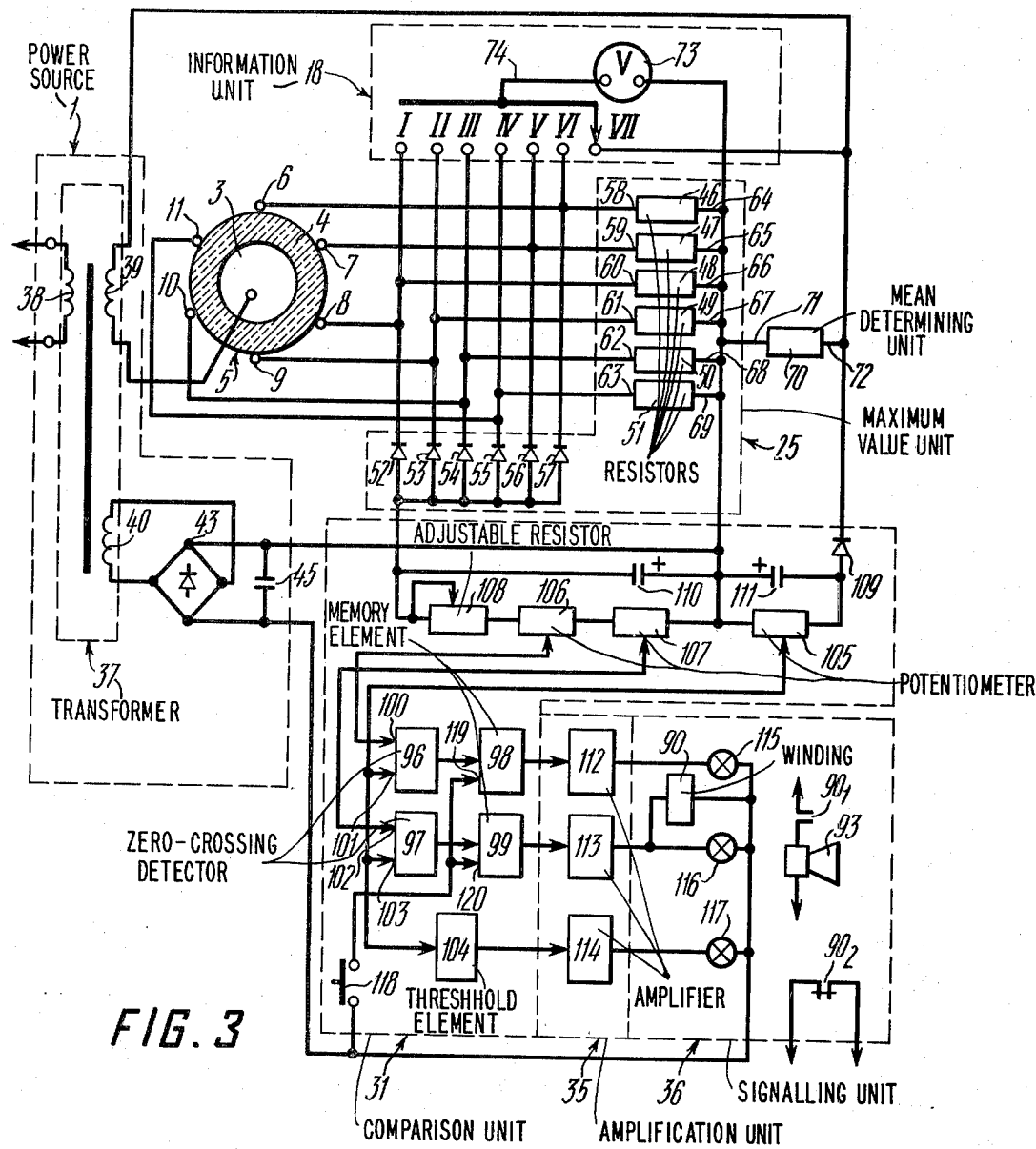
FIG. 3 is a schematic diagram of an alternative version of a device in accordance with the invention.

The device of FIG. 3 is similar to that of FIG. 2. The maximum value and the unit 25 mean determining unit 28 have the same circuitries as in the device of FIG. 2.

The two embodiments differ in that in the power source 1 of the second embodiment, the transformer 37 has only two secondary windings, 39 and 40; also the second embodiment has only one bridge rectifier 43 and one capacitor 45 which are connected to the winding 40.

The information unit 18 comprises a voltmeter 73 and one switch 74. The latter has seven positions designated in the drawing as I, II, III, IV, V, VI and VII.

The comparison unit 31 comprises two circuits, each including a zero-crossing detector, 96 or 97, of memory elements 98 and 99, respectively. Each of the zero-crossing detectors 96 and 97 has two inputs, 100 and 101 and 102 and 103, respectively. The inputs 101 and 103 are connected to a threshold element 104 and a potentiometer 105.

The inputs 100 and 102 of the zero-crossing detectors 96 and 97 are respectively connected to potentiometers 106 and 107 which are serially interposed between the potentiometer 105 and an adjustable resistor 108.

The resistor 108 is connected to the combined plates of the diodes 52, 53, 54, 55, 56 and 57 of the maximum value unit 25.

The potentiometer 105 is connected to the plate or anode of a diode 109. The cathode of the diode 109 is connected to the lead 72 of the resistor 70 and to the secondary winding 39 of the transformer 37.

Placed in parallel with the potentiometers 105, 106 and 107 and the resistor 108 are capacitors 110 and 111, which serve as smoothing filters.

The amplification unit 35 comprises three semiconductor amplifiers 112, 113 and 114. The amplifiers 112, 113 and 114 are connected to the outputs of the memory elements 98 and 99 and the threshold element 104, respectively.

The signalling unit 36 includes only one relay having a winding 90 with contacts $90_1$ and $90_2$, which actuates an audio indicator, i.e. a siren 93, and disconnects the power source (not shown) of the melting unit 5 in case an alarm signal is given.

Light signals "Danger," "Breakdown" and "General Wear" are given by switching on lamps 115, 116 and 117 connected to the outputs of the amplifiers 112, 113 and 114, respectively.

After the signalling unit 36 has been actuated, it is brought back to the initial state with the aid of a button 118 incorporated in the comparison unit 31. The buttom 118 is electrically coupled to control inputs 119 and 120 of the memory elements 98 and 99, respectively.

Figure 4:
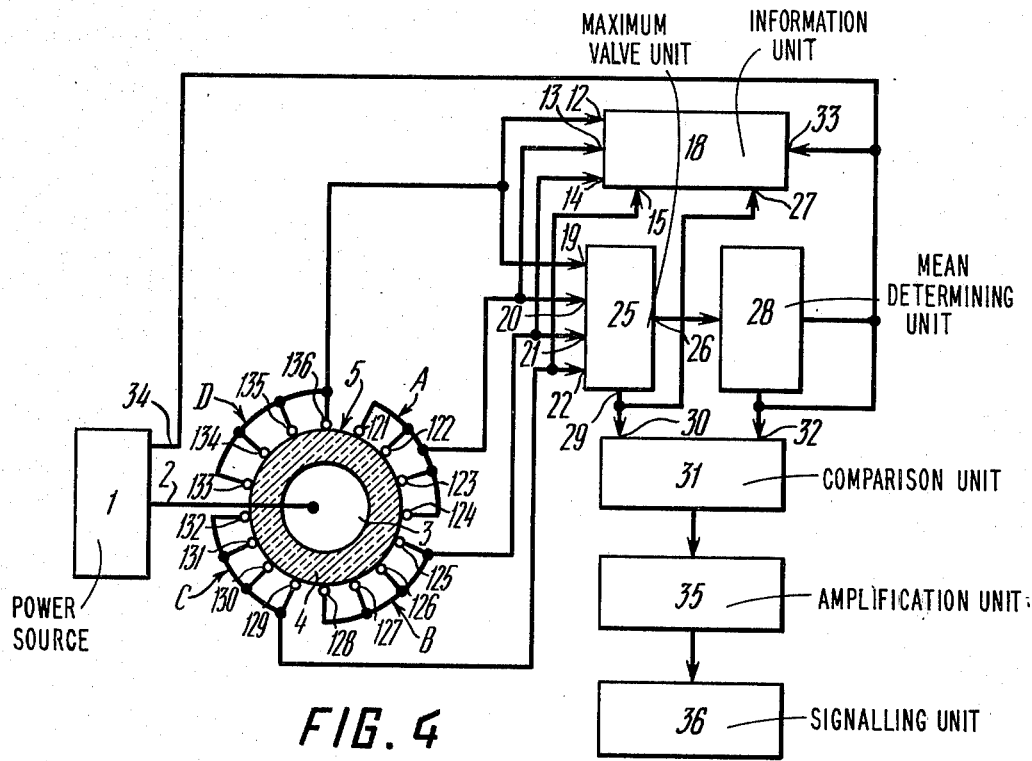
FIG. 4 is a block diagram showing the way of connecting the electrodes of the device to an information unit and to a maximum value unit, in accordance with the invention.

Unlike the devices of FIGS. 1 and 2, the device of FIG. 4 is intended for checking the state of lining of large-capacity melting units 5, where it is necessary to install large quantities of electrodes 121, 122, 123, 124, 125, 126, 127, 128, 129, 130, 131, 132, 133, 134, 135 and 136.

In this device, each four adjacent electrodes, i.e. 121, 122, 123 and 124, 125, 126, 127 and 128, 129, 130, 131 and 132, 133, 134, 135 and 136, are interconnected to form groups A, B, C and D, respectively. Each of the groups A, B, C and D is connected to a respective input 13, 14, 15 and 12 of the information unit 18 and to a respective input 20, 21, 22 and 19 of the maximum value unit 25. This circuitry configuration simplifies the information unit 18 and the maximum value unit 25 reducing the number of inputs, i.e. 12, 13, 14, 15 and 19, 20, 21, 22, as well as number of the resistors, i.e. 46, 47, 48, 49 (FIG. 3), as compared to the embodiments described above.

Figure 5:
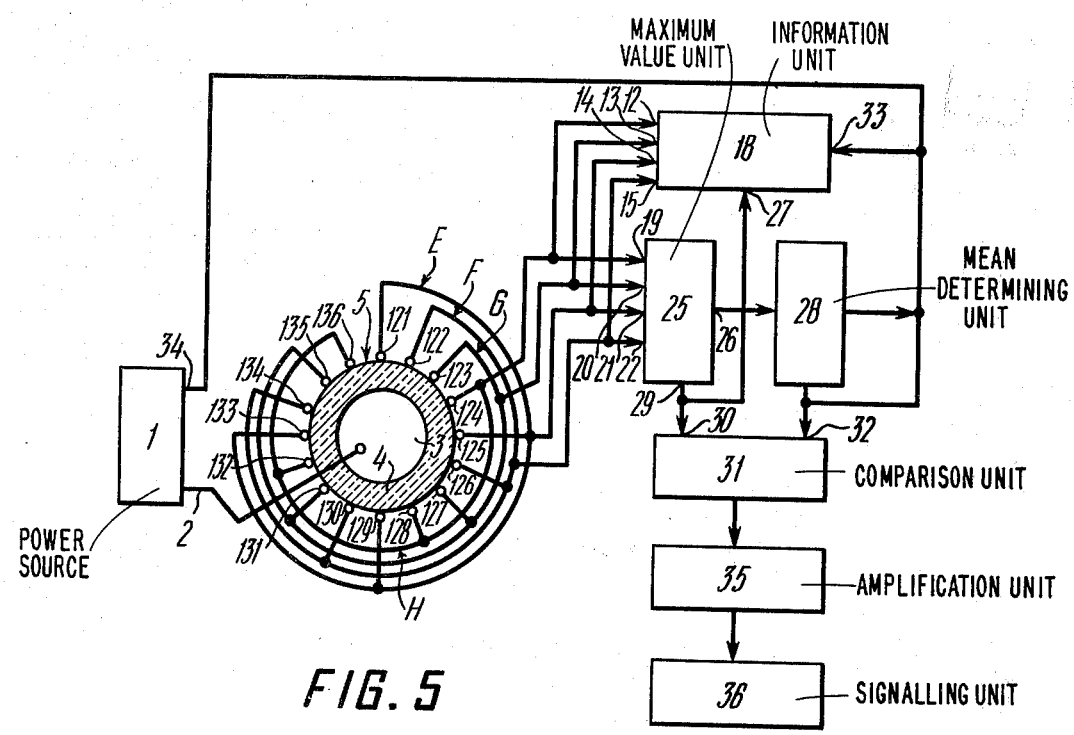
FIG. 5 is a block diagram showing an alternative way of connecting the electrodes of the device to the information unit and to the maximum value unit, in accordance with the invention.

The device of FIG. 5 is also intended for checking the state of the lining 4 of large-capacity melting units 5. In this embodiment, the inputs 14, 15, 13 and 12 of the information unit 18 and the inputs 21, 22, 20 and 19 of the maximum value unit 25 are also connected to respective groups E, F, G, H of the electrodes 121, 122, 123, 124, 125, 126, 127, 128, 129, 130, 131, 132, 133, 134, 135 and 136.

Group E includes the electrodes 121, 125, 129 and 133; group F includes the electrodes 122, 126, 130 and 134; group G includes the electrodes 123, 127, 131 and 135; and group H includes the electrodes 124, 128, 132 and 136. Thus the electrodes 121, 125, 129 and 133, 122, 126, 130 and 134, 123, 127, 131 and 135, and 124, 128, 132 and 136 of groups E, F, G and H, respectively, are spaced along the entire external surface of the lining 4 at different distances from one another. This raises the accuracy of checking the state of the lining 4 by compensating for the differences in the resistance of portions that are far apart, which differences are due to the non-uniformity of the fractional composition, as well as the non-uniformity of baking of individual layers of the lining 4.

The foregoing devices for carrying out the proposed method for checking the state of the lining 4 of the melting unit 5 operate as follows.

As the power source 1 (FIG. 1) is switched on, through the equal portions of the lining 4, located along the perimeter of the melting unit 5, there flow currents whose intensity is directly proportional to the electrical conductivity of said portions of the lining 4. If the state of the lining 4 is normal and if it is baked uniformly, the current intensities differ very little.

In such a case, the voltage across the output 29 of the maximum value unit 25 (the electrical conductivity of portions of the lining 4), which is applied to the input 30 of the comparison unit 31, differs by very little from the voltage across the output of the mean determining unit 28, which is applied to the input 32 of the comparison unit 31. In this case, at the outputs of the comparison unit 31 and the amplification unit 35 there are small voltages which are insufficient to actuate the signalling unit 36.

In case of damage of one or more portions of the lining 4, the intensity of currents flowing through the damaged portions increases due to a decrease in the resistance of these portions, whereas there is no change in the intensity of the currents flowing through all the other portions of the lining 4. As a result, there is an increase in the voltages across the outputs of the units 25 and 28. However, the increment in the voltage across the output 29 of the maximum value unit 25 is greater than the increment in the voltage across the output of the mean determining unit 28. As a result, at the output of the comparison unit 31 there is produced a voltage which is proportional to the difference in, or the quotient of the division of, said voltages. This voltage is amplified by the amplification unit 35 and applied to the input of the signalling unit 36.

If the output voltage of the amplification unit 35 reaches a first preset level, a "Danger" signal is produced at the output of the signalling unit 36. Further deterioration of the damaged portion of the lining 4 brings about a greater difference in the intensity of the current flowing through this damaged portion and the intensity of currents flowing through all the intact portions of the lining 4; hence, there is an increase in the output voltages of the comparison unit 31 and the amplification unit 35.

At a moment the voltage across the output of the amplification unit 35 reaches a second preset level, the unit 36 produces a "Breakdown" signal and disconnects the power source (not shown) of the melting unit 5.

The location of the damaged portion of the lining 4 is determined with the aid of the information unit 18.

The proposed method increases the accuracy of detecting local damage of the lining 4 of the melting unit 5 by to measuring the electrical parameters of limited portions of the lining 4, whose area is much smaller than that of the whole lining 4. The presence in the proposed device of the information unit 18 makes it possible to pinpoint the damaged portion of the lining 4; for this reason, the device of this invention compares favorably with similar conventional devices.

Uniform overall wear of the lining 4 brings about an increase in the intensity of currents flowing through all its portions, which results in an increase in the voltages across the outputs of the units 25 and 28. As voltage across the output 32 of the comparison unit 31 reaches a certain level, at the outputs of the comparison unit 31 and the amplification unit 35 there are produced electric signals which actuate the signalling unit 36 so that a "Danger" signal is produced at the signalling unit's output. The nature of the damage is determined by the information unit 18.

The method of this invention increases the accuracy of checking overall wear of the lining 4 of the melting unit 5 because the parameter being measured is the difference between, or the quotient of, the division of the maximum value and the arithmetic mean of the electrical conductivity value of portions of the lining 4. The parameter being measured depends very little on such factors as the temperature, humidity and density of the lining 4, as well as the baked layer thickness.

The device of FIG. 2 effects the proposed method for checking the state of the lining 4 of the melting unit 5 in the following manner.

Upon switching on the power source 1, from one of the resistors 46, 47, 48, 49, 50 and 51 connected to the respective electrodes 6, 7, 8, 9, 10 and 11 there is taken a voltage which is proportional to the maximum electrical conductivity of portions of the lining 4. A voltage, which is proportional to the arithmetic mean of the electrical conductivity of the lining's portions, is taken off the resistor 70. Said voltages are applied to the control windings 77 and 78 of the magnetic amplifier, which are placed in opposition. The difference in the ampere-turns of the windings 77 and 78 determines the moment of saturation of the working windings 82 and 83 of the magnetic amplifier, as well as the value of its output voltage.

If the lining 4 is intact, the bias winding 87 and the adjustable resistor 88 reduce the output voltage of the magnetic amplifier to almost zero.

If the lining 4 is damaged and the resistance of its damaged portion is reduced to 0.3 to 0.2 of the initial value, the contacts $89_1$ of the relay are closed, and the lamp 91 of the signalling unit 36 is switched on.

As the damaged portion of the lining 4 continues to deteriorate and its resistance is reduced to 0.1 to 0.08 of the initial value, the contacts $90_1$ and $90_2$ of the relay are closed, and the contact $90_3$ is broken. This switches on the lamp 92 and the siren 93 and the power source (not shown) of the melting unit 5 is disconnected.

The operation thresholds of said relays of the signalling unit 36 are set in advance, without actually connecting the melting unit 5 to the device of this invention, by simulating the resistances of portions of the lining 4 with the aid of adjustable resistors (not shown).

The damaged portion of the lining 4 is located with the aid of the information unit 18, by changing the positions of the switch 74 and reading out the indications of the voltmeter 73 related to different positions of the switch 74. The number and location of the damaged portion of the lining 4 correspond to the position I, II, III, IV, V, VI or VII of the switch 74, at which the voltemeter shows the maximum voltage.

Continued uniform overall wear of the lining 4 leads to an increase in the voltage taken off the resistor 70 and applied to the control winding 78 of the magnetic amplifier. When this voltage is equal to the stabilization voltage of the avalanche diode 81, there starts a flow of current through the latter. As a result, there is an increase is the voltage taken off the resistor 70 and applied to the winding 78 of the magnetic amplifier. This eventually leads to the closing of the contact $89_1$ of the relay, whereby the lamp 91 of the signalling unit 36 is switched on, and then to the closing of the contacts $90_1$ and $90_2$; the lamp 92 is switched on, and the siren 93 is brought into action; the contacts $90_1$ are broken, and the power source (not shown) is disconnected from the melting unit 5. In this case, the voltmeter 73 registers approximately the same voltages at all positions I, II, III, IV, V, VI and VII of the switch 74, which is indicative of uniform overall wear of the lining 4. By changing the position of the switches 75 and 76 with respect to the position of FIG. 2, one can measure the voltage which is proportional to the arithmetic mean of the electrical conductivity of the portions of the lining 4, which corresponds to the overall wear of the lining 4.

The device of FIG. 3 carries out the proposed method of checking the state of the lining 4 of the melting unit 5 in a similar manner.

In this case, the power source 1 feeds alternating current to the device. During one half-period of the supply voltage, an electric signal is applied from the output 29 (FIG. 1) of the maximum value unit 25 to the input 30 of the comparison unit 31 and to the capacitor 110 (FIG. 3). From the plate or anode of the capacitor 110, d.c. voltage is applied to the serially connected resistor 108 and potentiometers 106 and 107. During another half-period of the supply voltage, an electric signal is applied from the output of the mean determining unit 28 (FIG. 1) to the input 32 of the comparison unit 31 and to the capacitor 111 (FIG. 3). From the plate or anode of the capacitor 111, d.c. voltage is applied to the potentiometer 105.

At the inputs 100 and 101 of the zero-crossing detector 96, there are compared the voltage drops of voltages taken off the potentiometers 106 and 105; at the inputs 102 and 103 of the zero-crossing detector 97, there are compared the voltage drops of voltages taken off the potentiometers 107 and 105.

The voltage drops at the potentiometers 106 and 107 are proportional to the maximum electrical conductivity of the portions of the lining 4, which correspond to "Danger" and "Breakdown" signals. By moving the cursor of the potentiometer 106, one can change the voltage drop at said potentiometer 106, which corresponds to the "Danger" signal. By moving the cursor of the potentiometer 107, one can change the voltage drop at said potentiometer 107, corresponding to the "Breakdown" signal.

By varying the resistance of the resistor 108, one can simultaneously change the voltage drops at the potentiometers 106 and 107, corresponding to the "Danger" and "Breakdown" signals.

The voltage drop at the potentiometer 105 is proportional to the arithmetic mean of the electrical conductivity of the portions of the lining 4, corresponding to the "Overall Wear" signal. By moving the cursor of the potentiometer 105, one can change said voltage drop.

The cursors of the potentiometers 105, 106 and 107 are set so as to produce a voltage difference, in case of the normal state of the lining 4, across the inputs 100 and 101 and 102 and 103 of the respective zero-crossing detectors 96 and 97.

In case of a local damage of the lining 4, when the resistance of the damaged portions is reduced to 0.3 to 0.2 of the initial value, the voltage difference at the inputs 100 and 101 of the zero-crossing detector 96 becomes equal to zero. At the output of the zero-crossing detector 96 there appears an electric signal which actuates the memory element 98, the amplifier 112 and the lamp 115, so that at the output of the signalling unit 36 there is produced a "Danger" signal.

If the state of the lining 4 continues to deteriorate and the resistance of its damaged portions drops to 0.1 to 0.08 of the initial value, the voltage difference at the inputs 102 and 103 of the zero-crossing detector 97 becomes equal to zero. As a result, at the output of the zero-crossing detector 97 there is produced an electric signal which actuates the memory element 99, the amplifier 113 and the lamp 116, so that a "Breakdown" signal is produced at the output of the signalling unit 36. As this takes place, the contact $90_1$ of the relay is closed, whereby the siren 93 is brought into action; the contact $90_2$ is opened, whereby the power source (not shown) of the melting unit 5 is disconnected.

The signalling unit 36 is brought back to its initial state by pressing the button 118 and applying a reset signal to the control inputs 119 and 120 of the memory elements 98 and 99, respectively.

In case of a considerable overall wear of the lining 4, the voltage drop at the potentiometer 105, proportional to the arithmetic mean of the electrical conductivity of the portions of the lining 4 and applied to the input of the threshold element 104, reaches a level which is high enough to actuate said threshold element 104. As a result, at the output of the threshold element 104 there is produced a signal which is amplified by the amplifier 114 and switches on the lamp 117, so that at the output of the signalling unit 36 there is produced an "Overall Wear" signal.

The proposed method, carried out with the aid of the device of FIG. 3, accounts for a highly accurate assessment of the state of the lining 4. This is due to the fact that the device is supplied with alternating current, whereby the effects of polymerization of the material of the lining 4 upon the electrical conductivity of its portions are reduced.

This device makes it possible to simplify the information unit 18, as compared to the device of FIG. 2, since in the device of FIG. 3 the information unit 18 includes only one switch 74. As the switch 74 is set in position VII, the voltmeter 73 indicates the voltage which is proportional to the arithmetic mean of the electrical conductivity of the portions of the lining 4.

The device of FIG. 3 is advantageous in the case of induction furnaces operating at increased frequencies (from 1 to 8 kc) and having low-conductivity linings. In this case the frequency of the alternating current which powers the furnace substantially differs from that of the alternating current of the power source 1, and high-frequency interference is easily filtered by additional capacitors (not shown) placed in parallel with the diodes 52, 53, 54, 55, 56 and 57 of the maximum value unit 25.

The employment in the proposed device of the zero-crossing detectors 96 and 97, possessing high input resistances and incorporated in the comparison unit 31, makes it possible to increase the sensitivity of the device, which is essential in checking the state of a lining 4 manufactured from a low-conductivity material.

The devices of FIGS. 4 and 5 effect the proposed method of checking the state of the lining 4 of the melting unit 5 like the devices that are described above.

What is claimed is:

1. A device for checking the state of a lining of a melting unit, comprising: a power source having a first terminal connected to the metal in said melting unit and a second terminal; electrodes uniformly spaced on said lining along the perimeter of said melting unit; a maximum value unit, for determining the maximum value of a parameter being measured, having a group of inputs connected to respective electrodes and first and second outputs; a mean determining unit, for determining the arithmetic mean of the parameter being measured, having an input connected to the first output of said maximum value unit, and an output; an information unit, providing information on the state of said lining and having a group of inputs connected to respective electrodes, a first additional input connected to said first output of said maximum value unit, and a second additional input connected to the output of said mean determining unit and to the second terminal of said power source; a comparison unit, for comparing the maximum value and the arithmetic mean of the parameter being measured, having a first input connected to said second output of said maximum value unit, a second input connected to the output of said mean determining unit, and an output; an amplification unit having an input connected to the output of said comparison unit and an output; and a signalling unit having an input connected to the output of said amplification unit.

2. A device as claimed in claim 1, wherein said maximum value unit comprises: resistors having equal resistances, a first lead of each of said resistors being connected to a respective electrode, a second lead of each of said resistors being combined and connected to said first output of said maximum value unit; and diodes having a cathode connected to a respective electrode and an anode connected to said second output of said maximum value unit; and wherein said mean determining unit includes a resistor which has a resistance less than that of said resistors of said maximum value unit by a number of times equal to the number of said electrodes, a first lead of said resistor being connected to said input of said mean determining unit, and a second lead of said resistor being connected to said output of said mean determining unit.

3. A device as claimed in claim 1, wherein said comparison unit comprises a magnetic amplifier having control windings; and wherein said amplification unit comprises a magnetic amplifier with a working winding.

4. A device as claimed in claim 1, wherein said comparison unit comprises two zero-crossing detectors and a threshold element operatively associated together; and wherein said amplification unit comprises two semiconductor amplifiers connected to respective zero-crossing detectors and a third semiconductor amplifier connected to said threshold element.

5. A device as claimed in claim 1, wherein said electrodes are divided into groups of equal number of electrodes, the electrodes in each group being interconnected and connected to a respective input of the information unit and of the maximum value unit.

6. A method of checking the state of a lining of a melting unit, comprising the steps of: positioning a plurality of electrodes on the lining along the periphery of the melting unit; determining the maximum value of an electrical parameter of said lining by measuring the voltages of the electrodes; determining the arithmetic mean of said electrical parameter of said lining by measuring the voltages of the electrodes; and determining the state of said lining by comparing the maximum value and the arithmetic mean, a large difference between said maximum value and said mean indicating damage to said lining.

7. A method of checking the state of a lining of a melting unit according to claim 6, further comprising the step of: generating an alarm when the lining is damaged.

8. A method of checking the state of a lining of a melting unit according to claim 6, further comprising the step of: determining the damaged portion of the lining by separately measuring the voltage of each electrode, the electrode having the maximum value being connected to the damaged portion of the lining.

9. A method of checking the state of a lining of a melting unit according to claim 8, further comprising the step of: generating an alarm when the lining is damaged.

10. A method of checking the state of a lining of a melting unit according to claim 6, wherein the electrodes are positioned uniformly on the lining along the periphery of the melting unit.

* * * * *